(12) United States Patent
Farrell et al.

(10) Patent No.: US 8,032,964 B2
(45) Date of Patent: Oct. 11, 2011

(54) BRUSH SECTION FOR AN ELECTRIC TOOTHBRUSH

(75) Inventors: Mark Edward Farrell, Medfield, MA (US); Christopher Charles Blain, Petaluma, CA (US); Phillip Maurice Braun, Exeter, RI (US)

(73) Assignee: The Gillette Company, Boston, MA (US)

( * ) Notice: Subject to any disclaimer, the term of this patent is extended or adjusted under 35 U.S.C. 154(b) by 503 days.

(21) Appl. No.: 12/012,068

(22) Filed: Jan. 31, 2008

(65) Prior Publication Data

US 2008/0307591 A1    Dec. 18, 2008

Related U.S. Application Data

(60) Provisional application No. 60/899,280, filed on Feb. 2, 2007.

(51) Int. Cl.
*A61C 17/34* (2006.01)
*A61C 17/22* (2006.01)

(52) U.S. Cl. .............................. 15/22.1; 15/22.2; 15/22.4

(58) Field of Classification Search ................... 15/22.1, 15/22.2, 22.4, 23, 28
See application file for complete search history.

(56) References Cited

U.S. PATENT DOCUMENTS

| 1,517,320 | A | * | 12/1924 | Stoddart | 15/22.1 |
| 3,015,833 | A | * | 1/1962 | Gilet | 15/23 |
| 5,259,083 | A | * | 11/1993 | Stansbury, Jr. | 15/22.1 |
| 5,321,866 | A | * | 6/1994 | Klupt | 15/22.1 |
| 5,778,474 | A | * | 7/1998 | Shek | 15/22.1 |
| 6,892,412 | B2 | | 5/2005 | Gatzemeyer et al. | |
| 7,430,778 | B2 | | 10/2008 | Gatzemeyer et al. | |
| 2003/0140435 | A1 | | 7/2003 | Eliav et al. | |
| 2003/0140437 | A1 | | 7/2003 | Eliav et al. | |
| 2005/0000043 | A1 | | 1/2005 | Chan et al. | |
| 2008/0313830 | A1 | | 12/2008 | Gatzemeyer et al. | |
| 2009/0183324 | A1 | | 7/2009 | Fischer et al. | |

FOREIGN PATENT DOCUMENTS

| DE | 35 44 256 A1 | | 6/1987 |
| JP | 5-146314 | * | 6/1993 |
| JP | 10-66704 | * | 3/1998 |

OTHER PUBLICATIONS

PCT International Search Report dated Jun. 24, 2008.

* cited by examiner

*Primary Examiner* — Mark Spisich
(74) *Attorney, Agent, or Firm* — John P. Colbert; Vladimir Vitenberg

(57) ABSTRACT

A brush section for use with an electric toothbrush includes a relatively large brush head portion having a generally rectangular shape, although oblong, elliptical and other such shapes having a length to width aspect ration greater than 1 may be employed. The brush head portion is secured to a shaft portion of the brush section that may be configured to couple to a handle section. The handle section may include an electric drive including drive shaft, and the drive shaft may couple to the brush head via a coupling member positioned within the shaft portion. The electric drive may impart a rotary, oscillating rotary-oscillating or other suitable drive motion to the drive shaft that is, in turn, imparted upon the brush head by virtue of the coupling member.

14 Claims, 13 Drawing Sheets

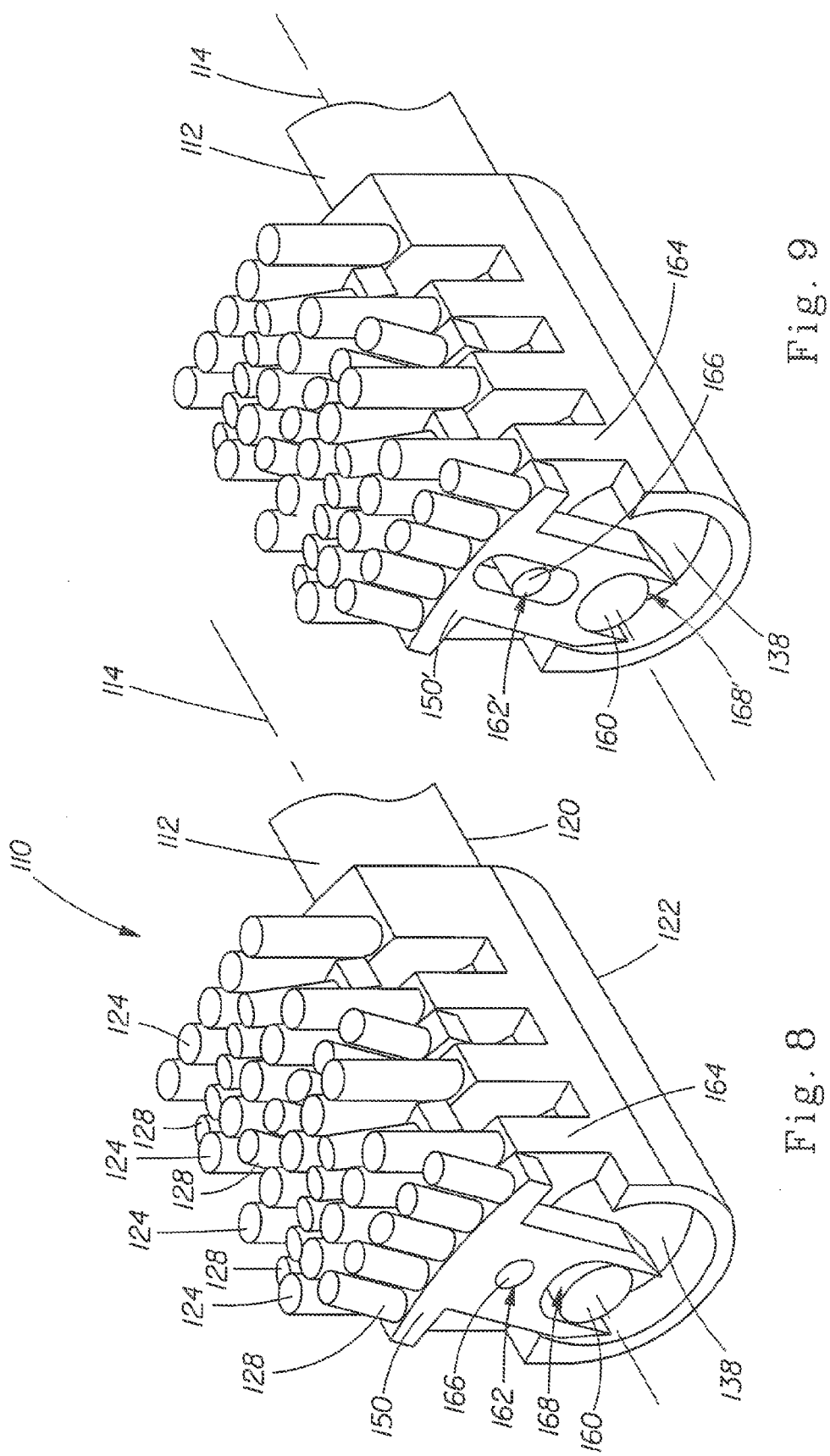

BRUSH SECTION FOR AN ELECTRIC TOOTHBRUSH

FIELD OF THE INVENTION

This application claims the benefit of U.S. Provisional Patent Application No. 60/899,280 filed on Feb. 2, 2007, which is incorporated here by reference. This patent relates to electric toothbrushes and in particular to a brush section for an electric toothbrush.

BACKGROUND OF THE INVENTION

An electric toothbrush may incorporate a brush section that couples to a handle section. A drive shaft may extend from the handle section with the drive shaft being coupled to an electric drive disposed within an interior of the handle section. The electric drive may impart a rotary, oscillating or combined rotary oscillating motion to the drive shaft so that the drive shaft is movable in a rotary or oscillating manner. The brush section can couple and secure to the handle section with the drive shaft coupling to a coupling element of the brush section, e.g., a shaft or drive pin. The motion of the drive shaft can be imparted upon the coupling element to provide a desired cleaning action to a brush head portion of the brush section.

A common arrangement for a brush section includes a substantially circular brush head portion. The brush head is caused, by action of the electric drive, to have a rotary or rotary-oscillating motion, i.e., cleaning motion during cleaning use. The circular brush head design combined with the cleaning motion is very effective for cleaning teeth and is optimal when a tooth-by-tooth cleaning pattern is used. Still, many consumers enjoy taking a proactive role in their oral hygiene activity. At times, the user will use the electric toothbrush with a manual brushing action, e.g., using vertical or circular strokes. For the electric toothbrush having a circular brush head design and employing a rotary or rotary-oscillating cleaning motion, using this electric toothbrush with a manual brushing action can be counter productive and may reduce the effectiveness of the brush head design and cleaning action. Ironically, the electric toothbrush is rendered less effective while the consumer erroneously believes the added action makes for a more effective and/or expedited cleaning process. Furthermore, years of training and conditioning have taught the consumer to use a circular or vertical cleaning motion, and habits may be difficult to change.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 8 is a schematic partial perspective view of an alternative brush head arrangement.

FIG. 9 is a schematic partial perspective view of a further alternative brush head arrangement.

DETAILED DESCRIPTION OF THE INVENTION

Figure 1:
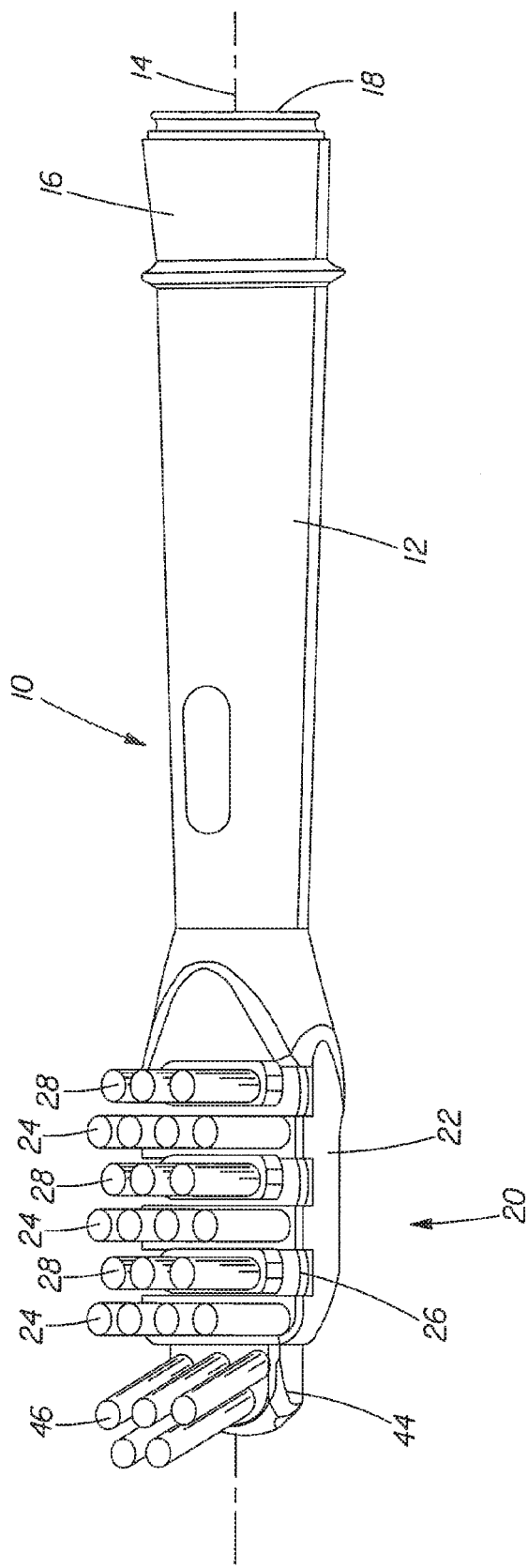
FIG. 1 is a schematic top view of a brush section in accordance with one embodiment.

A brush section for use with an electric toothbrush includes a brush head portion which may have a generally rectangular shape, although oblong, elliptical, or any suitable shape may be employed. Generally, the brush head portion may have a length-to-width aspect ratio greater than 1, although such an arrangement is not required. The brush head portion is secured to a tube member of the brush section that may be configured to couple to a handle section. The handle section may include an electric drive including a drive shaft, and the drive shaft may couple to the brush head via a coupling or drive pin member positioned within the tube member. In some embodiments, the electric drive may impart a rotary, oscillating, rotary-oscillating or other suitable drive motion to the drive shaft that is, in turn, imparted upon the brush head and bristle members thereof by virtue of the coupling member.

The brush head may incorporate a first plurality of cleaning bristles that are static, i.e., fixed relative to the brush head and a second plurality of cleaning bristles that are moveable in a cleaning motion relative to the first plurality of bristles. For example, the second plurality of cleaning bristles may include a bristle support structure or bristle holder that is supported within the brush head to have at least one direction of freedom to move relative to the brush head and the first plurality of bristles. In one embodiment, the bristle support structure may be free to pivot about a first axis relative to the brush head. The coupling member couples the bristle support structure to the electric drive for driving the bristle support structure causing the second plurality of bristles to have the desired cleaning motion. The bristle support structure may comprise a plurality of separate bristle support structures such that each structure may move independently with respect to each other separate bristle support structure. Furthermore, the cleaning motion may include an eccentric motion or translational motion in combination with a rotary, oscillating or other suitable cleaning motion.

It will be understood and appreciated that while various aspects, features and advantages of the invention are described in connection with particular embodiments, the herein described aspects, features and advantages may be implemented in any of the embodiments, and as such, the features and structures of the various embodiments may be mixed and matched yielding a virtually limitless number of combinations. One of skill in the art will furthermore appreciate that the herein described aspects, features and advantages of the invention may be combined with structures and devices known to or later discovered by the skilled artisan.

The herein described embodiments of brush sections are suited to operate in conjunction with an electric toothbrush, such for example, as an electric toothbrush of the type having a handle section including an electric drive and a drive shaft having a longitudinal axis. The electric drive imparts a motion to the drive shaft. It may, for example, impart a rotary, oscillating, or rotary and oscillating motion to the drive shaft. The motion of the drive shaft is coupled to the brush section to impart a desired motion to a brush head portion of the brush section such that the brush head portion, or any component thereof, is caused to have a desired cleaning motion. Many different kinds of cleaning motions, including rotary, oscillating, vertical and/or horizontal sweeping and the like, may be used. Generally, as used herein, cleaning motion describes any desired or effective movement of the bristles relative to the brush head to affect cleaning. Handle sections, as described above, are well known to the skilled artisan. In addition, the brush sections may be configured for use with such existing handle sections or may be configured with new handle sections types, as the case may be.

Figure 2:
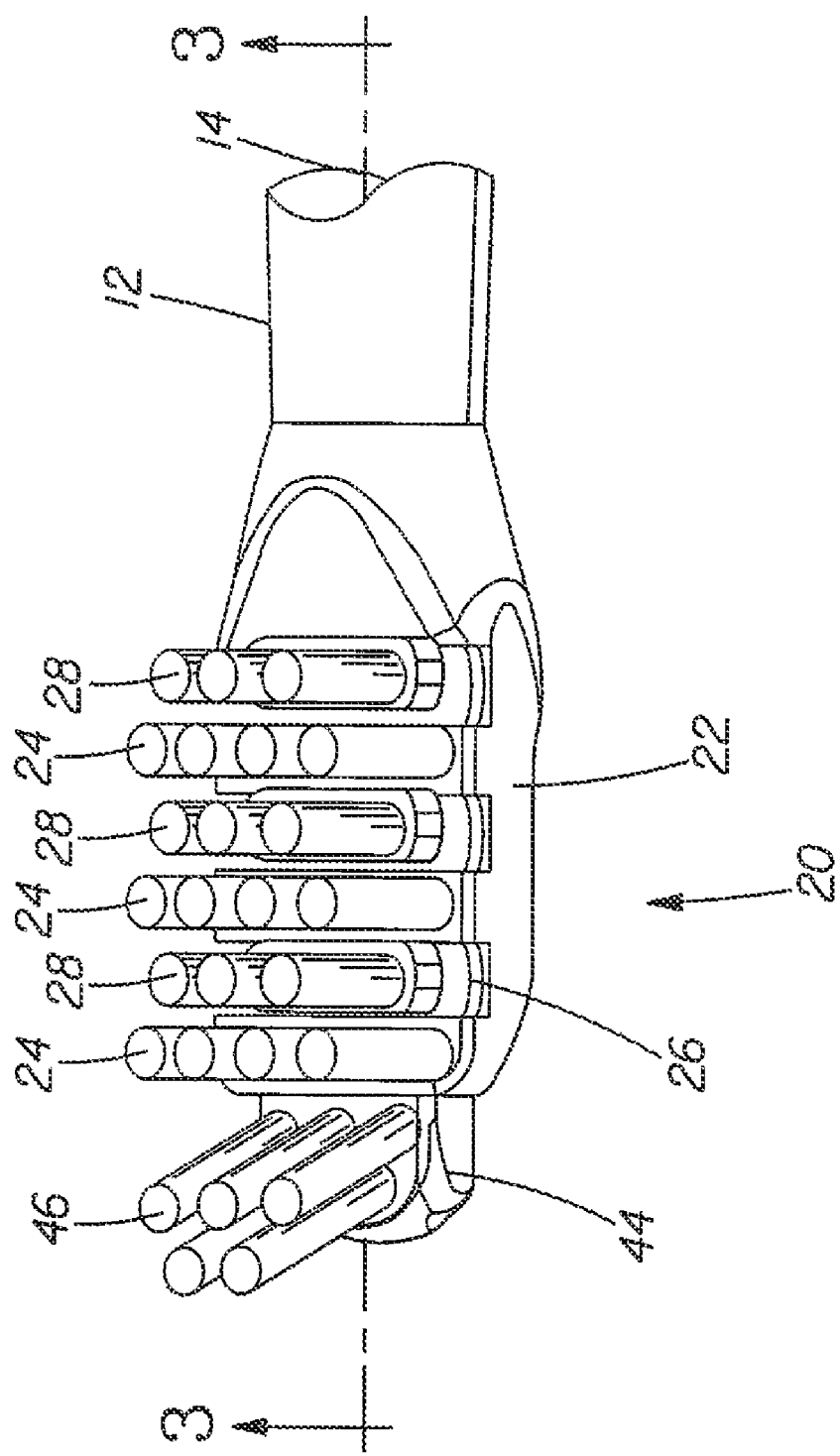
FIG. 2 is a schematic partial top view of a brush head portion of the brush section illustrated in FIG. 1.
Figure 3:
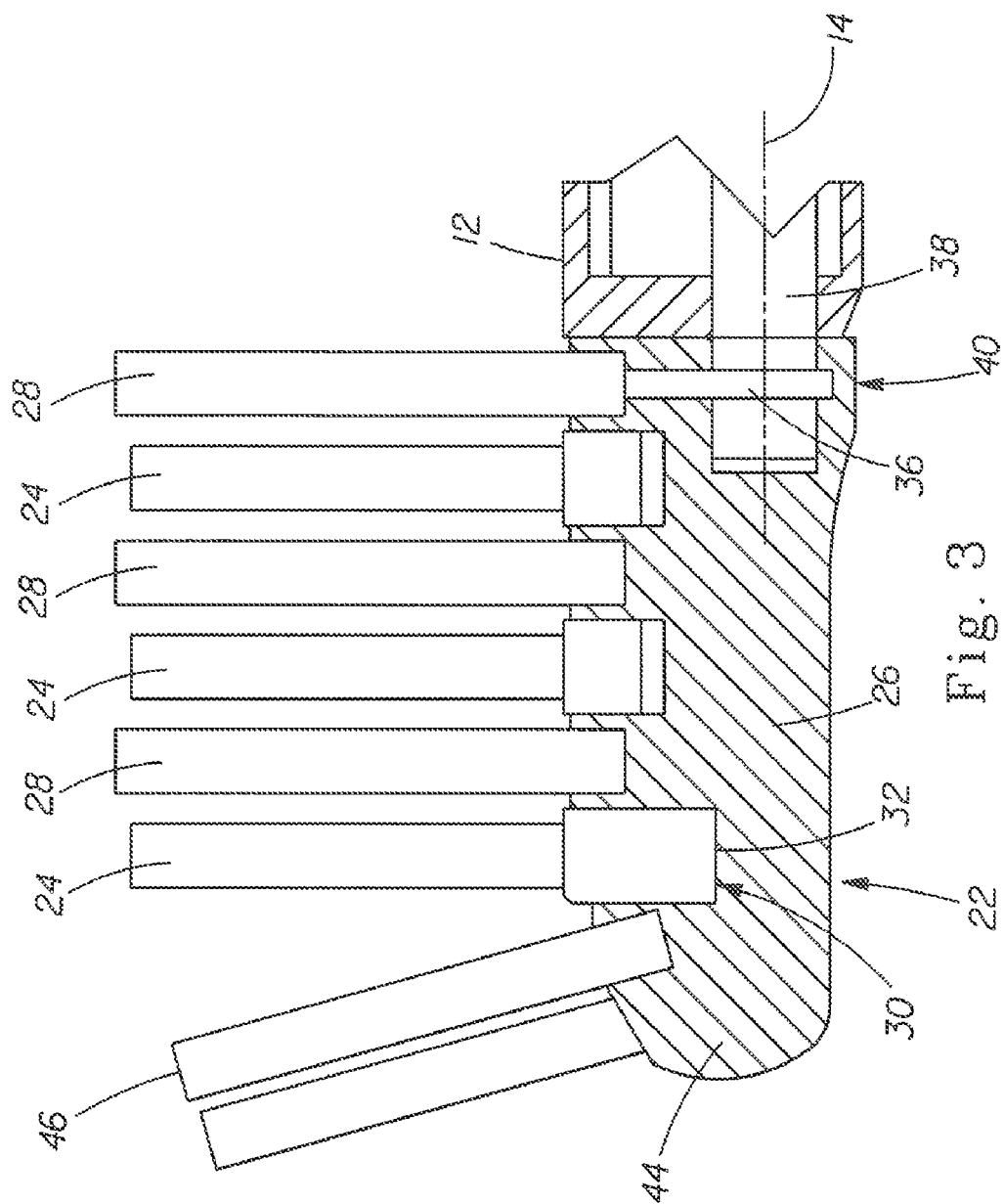
FIG. 3 is a schematic cross-section view of the brush head portion illustrated in FIG. 2.

FIGS. 1-3 illustrate a brush section 10 which may be push-fitted onto a toothbrush handle section and coupled to the drive shaft of the handle section, such for example, as a handle section described above. The brush section includes a mounting tube 12 extending along an axis 14. The axis 14 is a longitudinal axis of the cleaning section and may coincide with a longitudinal section of the drive shaft 38 (FIG. 3). At a first end 16 (FIG. 1), the mounting tube 12 may include a profile ring 18 having an inside contour complementary with an outside contour of the handle section. In this manner, the brush section 10 can be push-fitted onto the handle section in a manner preventing relative rotation of the brush section with respect to the handle section. A tab/slot, key/spline or other similar structure may be included in the corresponding contour surfaces to facilitate alignment of the brush section with the handle section and to further prevent relative rotation between the two.

At a second end 20 the brush section 10 includes a brush head portion 22. In some embodiments, the brush head portion 22 supports a first plurality of contact elements 24 that are mounted to the head portion 22 so as to be fixed, i.e., they are static relative to the head portion 22. Any suitable method of mounting the first plurality of contact elements 24 to the head portion 22 may be used. For example, where the contact elements 24 comprise a plurality of bristles, methods, such as hot tufting, gluing, stapling, and the like, may be utilized. As another example, where the contact elements 24 comprise a plurality of elastomeric elements, methods such as gluing, snap-fitting, welding, molding, etc. may be utilized.

Supported within the head portion 22 is a movable contact element support or moveable contact element holder 26 supporting a second plurality of contact elements 28. The second plurality of contact elements 28 may be mounted to the movable contact element holder 26 using any suitable method, as described above with regard to the first plurality of contact elements 24. The movable contact element holder 26 may be supported within the head portion 22 such that it is able to rotate about the longitudinal axis 14 responsive to a suitable driving input from the handle section.

The first plurality of contact elements 24 may have a first height and the second plurality of contact elements 28 may have a second height, different than the first height. Additionally, the ends of the first and second pluralities of contact elements 24 and 28 may have contoured, rounded or otherwise shaped ends. Among the first plurality of contact elements 24 and the second plurality of contact elements 28, contact elements or tufts of bristles (in embodiments where the contact elements comprise a plurality of bristles) at different locations of the head portion 22, e.g. front to back and/or center to edge, may also have different heights and different bristle end contours.

The first plurality of contact elements 24 may be arranged in rows transverse relative to the axis 14. Similarly, the second plurality of contact elements 28 may be arranged in rows transverse relative to the axis 14. In some embodiments, the transverse rows may alternate between rows of first plurality of contact elements 24 and rows of second plurality of contact elements 28. In some embodiments, multiple rows of the first plurality of contact elements may be separated by a row or multiple rows of the second plurality of contact elements 28 and vice versa or the rows may be interleaved or arranged in virtually any manner.

As shown in FIG. 3, in some embodiments, the head portion 22 may include a first bearing surface 30 that engages a recess, notch, slot or other suitable formation 32 formed in the movable contact element holder 26. As shown, in some embodiments, the recess, notch, slot, or other suitable formation 32 may be disposed between the second plurality of contact elements 28 and a third plurality of contact elements 46.

A drive shaft 38 may engage the movable contact element holder 26 such that movement of the drive shaft 38 can be transferred to the movable contact element holder 26. The drive shaft 38 may be supported within the mounting tube 12 at a rearward end 40 of the head portion 22. The drive shaft 38 may be joined to the contact element holder 26 via any suitable means. For example, as shown, the drive shaft 38 may be joined to the movable contact element holder 26 via a drive pin 36. As yet another example, the drive shaft 38 may be joined to the movable contact element holder 26 adhesively, chemically, mechanically, electrically, e.g. magnetic clutch, or any combination thereof. In some embodiments, the drive pin 36 may be inserted into the movable contact element holder 26 and/or the drive shaft 38 via corresponding apertures in the movable contact element holder 26 and/or drive shaft 38.

Figure 4:
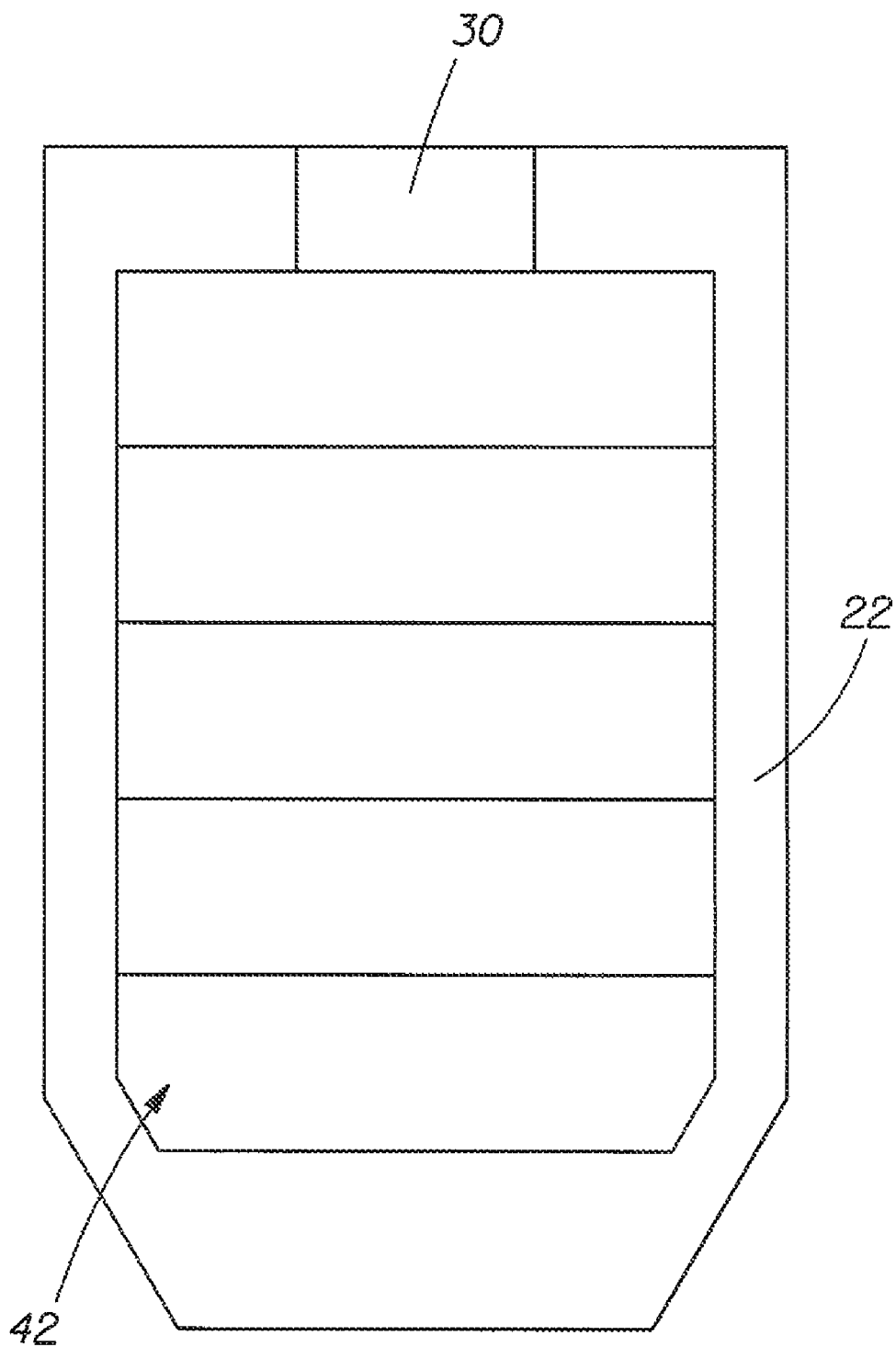
FIG. 4 is a schematic top view of the brush head portion of FIG. 2 with the cleaning element fields removed for visual facilitation.

As shown in FIG. 4, the movable contact element holder 26 (shown in FIGS. 1-3) may be snap-fitted into the head portion 22 via an opening 42. The opening 42 may then be closed with a snap-in-place housing member (not depicted).

In the embodiment shown in FIGS. 1-3, the movable contact element holder 26 may include an extension portion 44 supporting the third plurality of contact elements 46. The extension portion 44 may be supported to permit at least one freedom of motion relative to the head portion 22. For example, the extension portion 44 may be supported to rotate relative to the head portion 22. In this manner, the third plurality of contact elements 46 may move in a cleaning motion relative to the first plurality of contact elements 24 and/or the second plurality of contact elements 28. For example, the extension portion 44 may couple to the movable bristle holder 26 such that the third plurality of contact elements 46 moves in a similar manner as the second plurality of contact elements 28.

In other embodiments, the brush head portion 22 comprises the extension portion 44 and the third plurality of contact elements 46. In such embodiments, the third plurality of contact elements 46 may be stationary with respect to the brush head portion 22.

Referring back to FIG. 3, in some embodiments, the coupling between the extension portion 44 and the movable contact element holder 26 may be direct such that the extension portion 44 moves with the movable contact element holder 26. However, in some embodiments, the extension portion 44 may couple to the drive pin 38, directly, via a cam arrangement, a linkage or otherwise, and/or to the movable contact element holder 26 or otherwise such that the extension portion 44 has a cleaning motion that is separate from a cleaning motion of the movable contact element holder 26 and the second plurality of contact elements 28.

In the embodiment shown if FIGS. 1-3, the movable contact element holder 26 may oscillate about the axis 14 thereby causing the second plurality of contact elements 28 and/or the third plurality of contact elements 46 to similarly oscillate about the axis 14. The movement of the movable contact element holder 26 may cause the second plurality of contact elements 28 and/or the third plurality of contact elements 46 to oscillate back and forth angularly to provide a cleaning action substantially similar to an up-down manual brushing action.

The amount of angular movement as well as the speed exhibited by the movable contact element holder 26 and the second plurality of contact elements 28 and/or the third plurality of contact elements 46 can impact the efficacy of the cleaning action. Generally, oscillation angle within the range of 40-60 degrees is considered beneficial. For example, the movable contact element holder 26 may move through an angle of about 44 degrees, i.e., +/−22 degrees relative to the head portion 22, in some embodiments. Another example includes 55 degrees angle. However, any suitable angle may be utilized. For example, other angles greater than 55 degrees or less than 44 degrees may be used.

In some embodiments, the movable contact element holder 26 can move through an angle of from about 10 degrees to about 90 degrees, or any individual number within the range. In some embodiments, the movable contact element holder 26 can move through an angle greater than about 10 degrees, greater than about 12 degrees, greater than about 15 degrees, greater than about 18 degrees, greater than about 20 degrees, greater than about 22.5 degrees, greater than about 25 degrees, greater than about 30 degrees, greater than about 35 degrees, greater than about 40 degrees, greater than about 45 degrees, greater than about 50 degrees, greater than about 55, greater than about 60 degrees, greater than about 65 degrees, greater than about 70 degrees, greater than about 75 degrees, greater than about 80 degrees, greater than about 85 degrees, and/or less than about 90 degrees, less than about 85 degrees, less than about 80 degrees, less than about 75 degrees, less than about 70 degrees, less than about 65 degrees, less than about 60 degrees, less than about 55 degrees, less than about 50 degrees, less than about 45 degrees, less than about 40 degrees, less than about 35 degrees, less than about 30 degrees, less than about 25 degrees, less than about 22.45 degrees, less than about 20 degrees, less than about 18 degrees, less than about 15 degrees, less than about 12 degrees, or less than about 10 degrees.

As stated above, the speed at which the movable contact element holder 26 and the second plurality of contact elements 28 and/or the third plurality of contact elements 46 move through their angular movement may also impact the efficacy of the cleaning action. For example, a speed of about 75 Hz may provide adequate cleaning where the movable contact element holder 26 moves through an angle of about 44 degrees. In general, where the movable contact element holder 26 moves through the smaller angle, the speed at which the movable contact element holder 26 moves through the angle may increase in order to maintain cleaning efficacy.

The movable contact element holder 26 may move through its respective angle at a speed ranging from between about 30 Hz to about 130 Hz, or any individual number within the range. In some embodiments, the movable contact element holder 26 may move through its respective angle at a speed of greater than about 30 Hz, greater than about 40 Hz, greater than about 50 Hz, greater than about 60 Hz, greater than about 70 Hz, greater than about 80 Hz, greater than about 90 Hz, greater than about 100 Hz, greater than about 110 Hz, greater than about 120 Hz, and/or less than about 130 Hz, less than about 120 Hz, less than about 110 Hz, less than about 100 Hz, less than about 90 Hz, less than about 80 Hz, less than about 70 Hz, less than about 60 Hz, less than about 50 Hz, or less than about 40 Hz.

Advantageously, with the movement of the second plurality of contact elements 28 and/or the movement of the third plurality of contact elements 46, and a manually imparted cleaning movement of the overall head portion 22, the user may experience an enhanced and effective cleaning action. Furthermore, instead of the user's manual manipulation of the toothbrush incorporating the brush section 10 drawing away from, and degrading, the driven cleaning action, the two actions may combine to provide an enhanced cleaning affect. Also, in the event that the handle section becomes discharged and thus the electric drive becomes disabled, the brush section 10 may be easily used in the same manner as a manual toothbrush to affect cleaning.

In some embodiments, the brush section 10 may comprise a transponder, and the handle section may comprise a detector or a reading device as described in U.S. Patent Application Publication Nos. 2004/0255409 and 2003/0101526. The transponder can be configured to communicate information about the brush section 10 to the detector or reading device. The reading device or detector can be in signal communication with a controller which may be configured to control the speed of a motor and/or the angular motion of a shaft of the motor. The basic architecture of a controller, reading device, detector, and/or transponder is generally known.

The speed of the motor as well as the angle which of oscillatory shaft displacement can be controlled in any suitable manner. For example, one means of modifying the speed of the motor is to increase or decrease the voltage to the motor. Typically, an increase in voltage will increase the speed of the motor while a decrease in voltage will decrease the speed of the motor. Such mechanisms for modifying the voltage delivered to motors are well known. As another example, the speed of the motor may be modified via a transmission system.

Figure 11A:
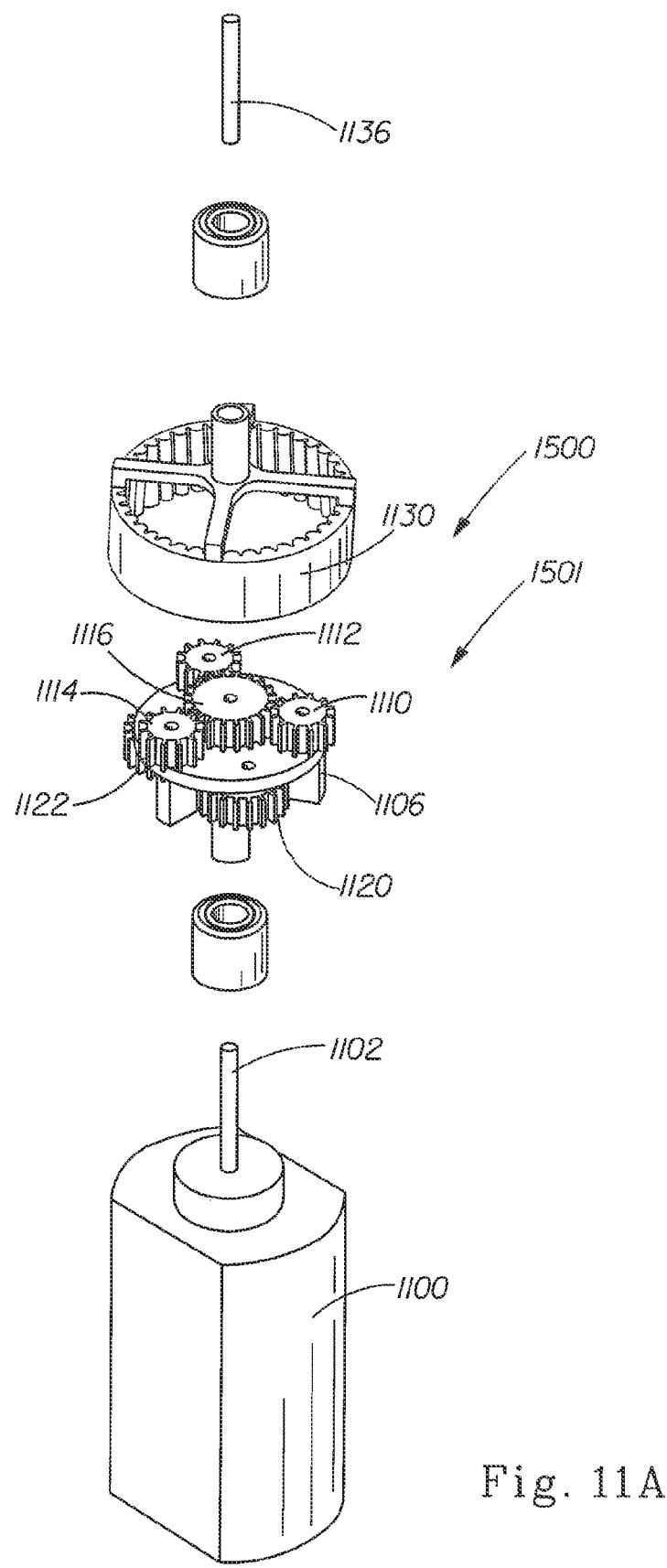
FIG. 11A is a schematic exploded view of a drive system suitable for use in the present invention.
Figure 11B:
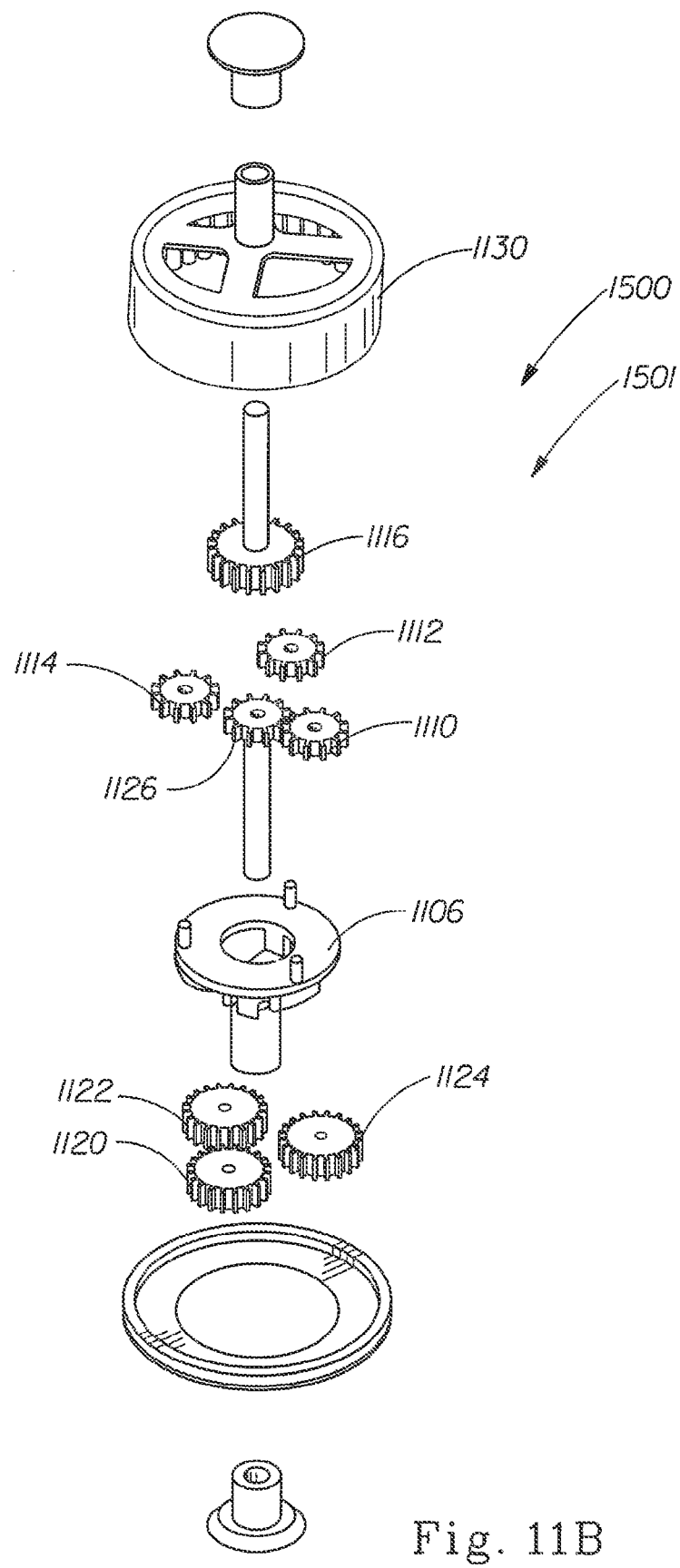
FIG. 11B is a schematic exploded view of the drive system of FIG. 11A.

FIGS. 11A and 11B illustrate one embodiment of a transmission system. A transmission system 1500 may comprise a drive system 1501. The drive system 1501 may comprise a motor 1100 having a shaft 1102. The shaft 1102 may be operatively connected to a first driver 1126 and/or a second driver 1116. In a first configuration, the teeth of the first driver 1126 may be intermeshed with teeth from a plurality of planetary gears 1120, 1122, and/or 1124. In a second configuration, the teeth of the second driver 1116 may be intermeshed with teeth from a plurality of planetary gears 1110, 1112, and/or 1114.

As shown, the first driver 1126 and/or the second driver 1116 as well as their respective planetary gears may be disposed on a gear carrier 1106. The planetary gears may be rotatably connected to the gear carrier 1106.

A ring gear 1130 may comprise complementary teeth to those of the planetary gears. As such, the teeth of the ring gear 1130 may intermesh with the teeth of the planetary gears. In some embodiments, an output shaft 1136 may be operatively connected to the ring gear 1130. In such embodiments, the ring gear 1130 may be driven at various speeds depending on the size of the driver gear and its respective planetary gears. For example, as shown, the first driver 1126 may have a smaller diameter than the second driver 1116. As such, the corresponding planetary gears, e.g. 1120, 1122, and/or 1124 may have larger diameters than the first driver 1126. So, in the first configuration, for a predetermined rotational speed of the motor shaft 1102, the ring gear 1130 may have a rotational speed which is less than the rotational speed of the motor shaft 1102. In contrast, in the second configuration, for a predetermined rotational speed of the motor shaft 1102, the ring gear 1130 may have a rotational speed which is greater than the rotational speed of the motor shaft 1102. In the second configuration, the second driver 1116 may have a diameter which is greater than the diameter of its respective planetary gears, e.g. 1110, 1112, and/or 1114. The selection of the first driver 1126 and/or the second driver 1116 may be created via a clutch system or any other suitable means.

In some embodiments, the first driver 1126 and/or the second driver 1116 may be operatively connected to the output shaft 1136. In such embodiments, the ring gear 1130 may be driven by the shaft 1102 while the gear carrier 1106 remains stationary. Alternatively, the gear carrier 1106 may be driven by the shaft 1102 while the ring gear 1130 remains stationary.

Figure 12A:
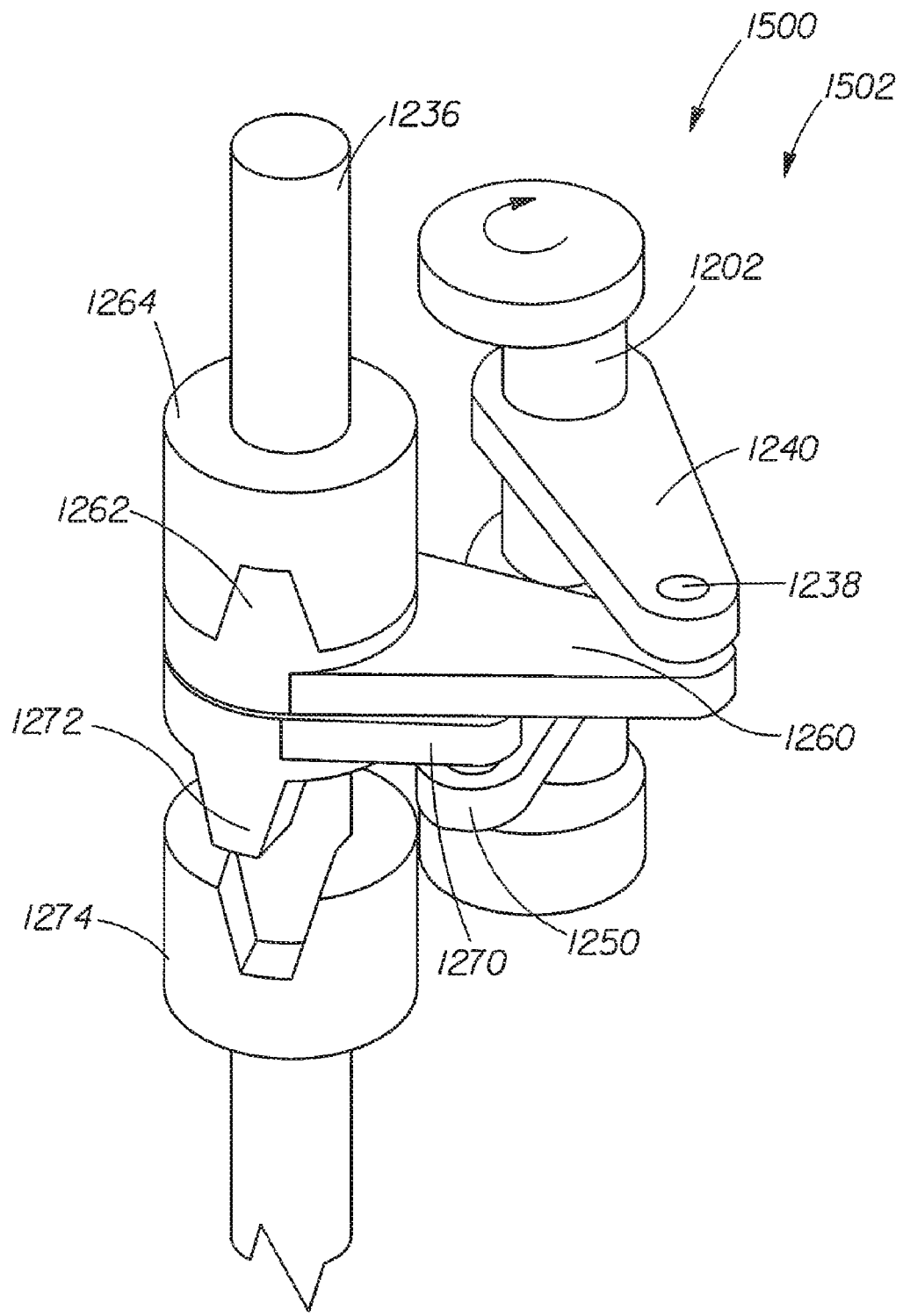
FIGS. 12A and 12B are schematic elevation views showing an output system suitable for use in the present invention.
Figure 12B:
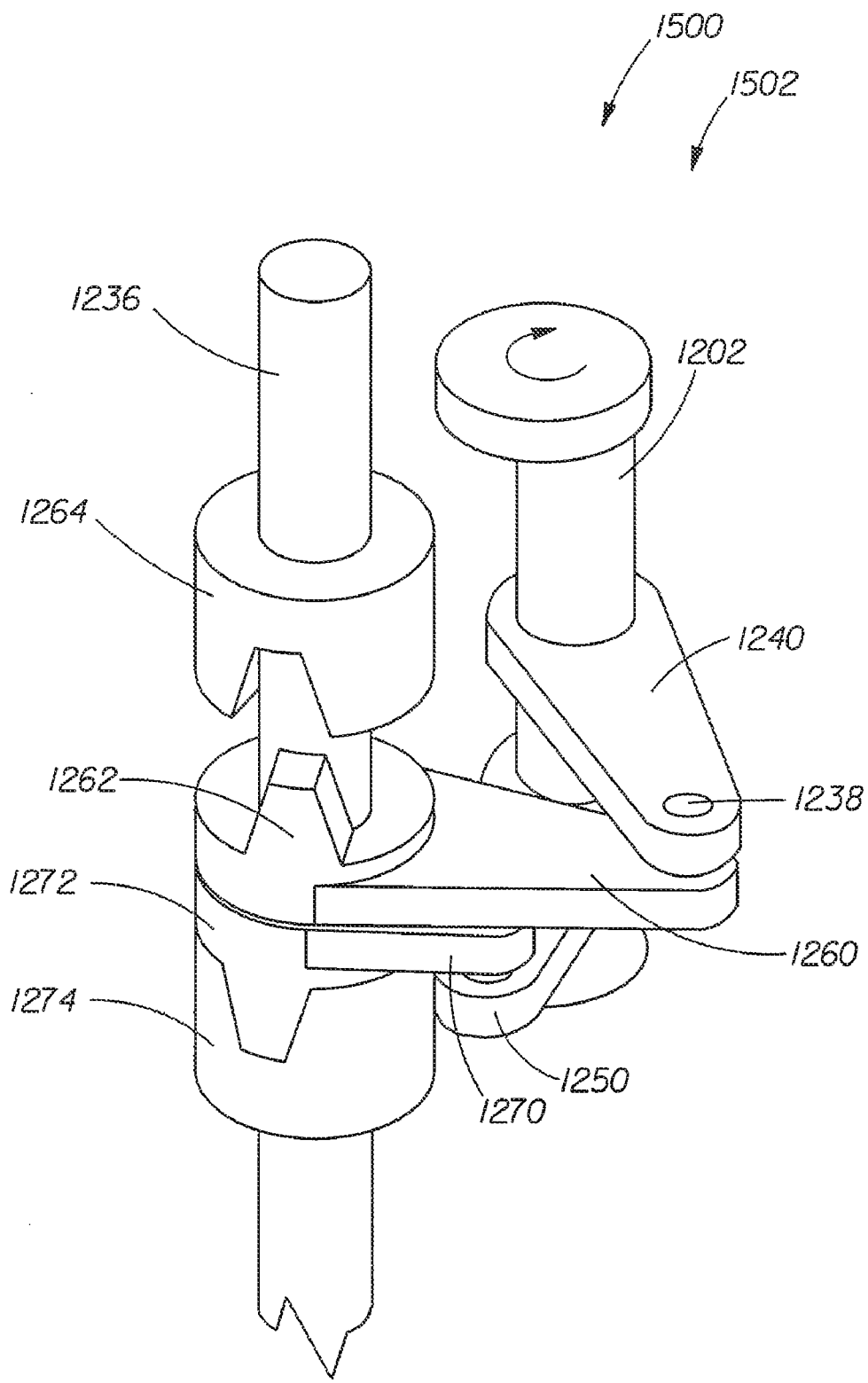

Additionally, as stated previously, the angle may be modified in any suitable manner. For example, as shown in FIGS. 12A and 12B, the transmission system 1500 may further comprise an output system 1502. Embodiments are contemplated where devices of the present invention include the drive system 1501 and/or the output system 1502.

As shown in FIGS. 12A and 12B, the output system 1502 may comprise a shaft 1202, a first driver linkage 1240, a first driven linkage 1260, a second driver linkage 1250, a second driven linkage 1270, and an output shaft 1236. The shaft 1202 may be operatively connected to a motor such that the shaft 1202 is driven by the motor. The first driver linkage 1240 and the second driver linkage 1250 may be connected to the shaft 1202 such that the first driver linkage 1240 and the second driver linkage 1250 are capable of rotating with respect to the shaft 1202.

The first driver linkage 1240 may be pivotally connected to the first driven linkage 1260 via pin 1238, in some embodiments. Similarly, the second driver linkage 1250 may be pivotally connected to the second driven linkage 1270 via a pin, in some embodiments.

The first driven linkage 1260 comprises at least one engagement element 1262 which is capable of intermeshing with a first receiving element 1264. As shown, the engagement element 1262 may comprise a tooth, and the receiving element 1264 may comprise a recessed area for receiving the tooth of the engagement element 1262. The receiving element 1264 may be fixed to the output shaft 1236 such that rotational motion imparted to the receiving element 1264 may thereby be transferred to the output shaft 1236.

Similarly, the second driven linkage 1270 may comprise at least one engagement element 1272 which is capable of intermeshing with a second receiving element 1274. The at least one engagement element 1272 of the second driven linkage 1270 and the second receiving element 1274 may be configured as described above with regard to the engagement element 1262 and receiving element 1264. The second receiving element 1274 may be fixed to the output shaft 1236 such that rotational motion imparted to the second receiving element 1274 may be transferred to the output shaft 1236.

The first driver linkage 1240 and the first driven linkage 1260 may have different lengths in order to impart a particular angular displacement to the output shaft 1236. In some embodiments, the first driver linkage 1240 and the first driven linkage 1260 may have equal lengths. The second driver linkage 1250 and the second driven linkage 1270 may be similarly configured. The analysis of the relative lengths of the linkages to achieve a particular displacement is founded on principles which are generally well known, e.g. four bar linkage analysis.

As shown in FIG. 12A, when the first engagement element 1262 is engaged with the first receiving element 1264, the output shaft 1236 may have a first angular displacement. The first angular displacement may be similar to the angular displacement described heretofore. In this configuration, the second engagement element 1272 may be disengaged with the second receiving element 1274.

As shown in FIG. 12B, when the second engagement element 1272 is engaged with the second receiving element 1274, the output shaft 1236 may have a second angular displacement. The second angular displacement may be similar to the angular displacement described heretofore. However, the first angular displacement may be different from the second angular displacement. For example, the first angular displacement may be greater than the second angular displacement. As another example, the first angular displacement may be less than the second angular displacement.

Figure 5:
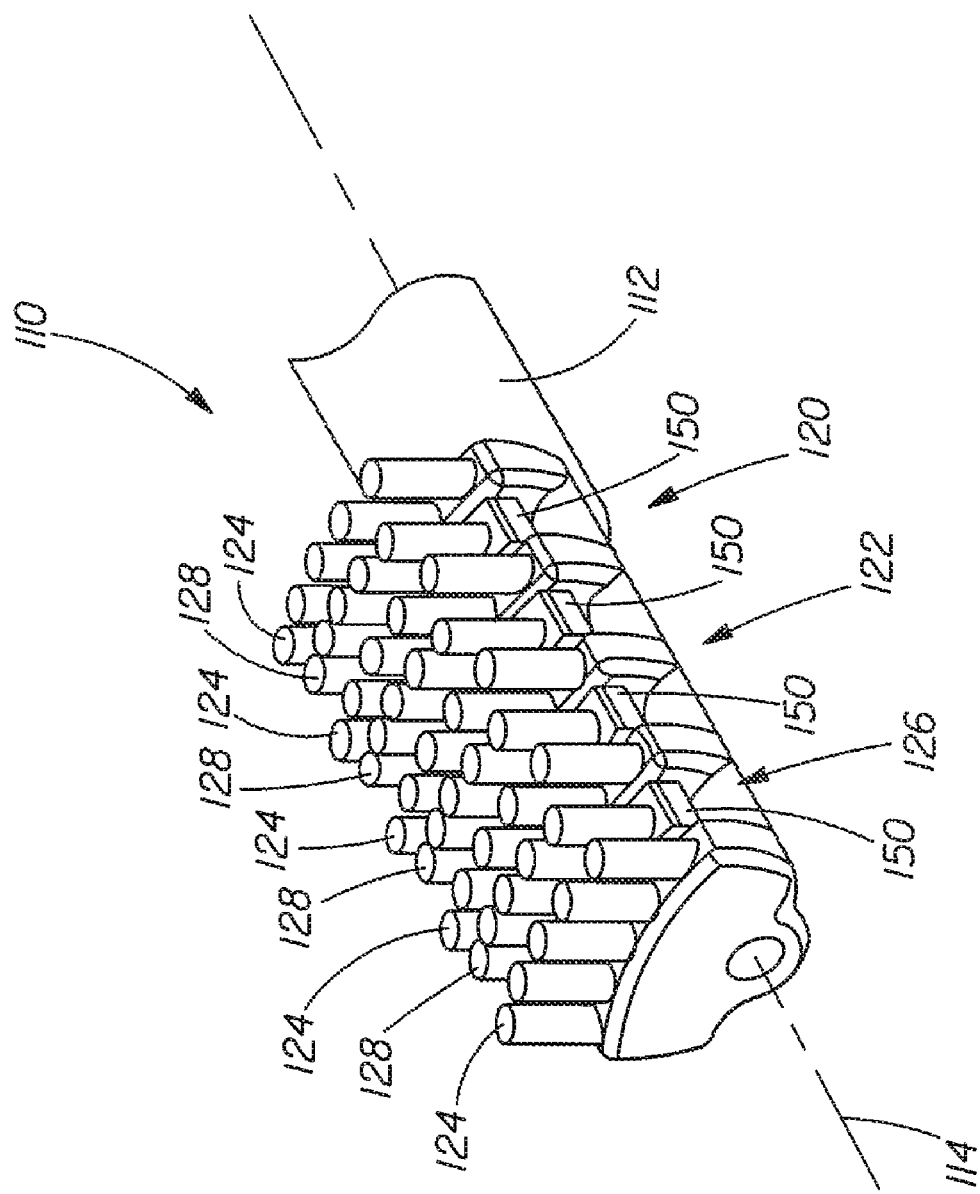
FIG. 5 is a schematic partial perspective view of a brush section in accordance with another embodiment.
Figure 6:
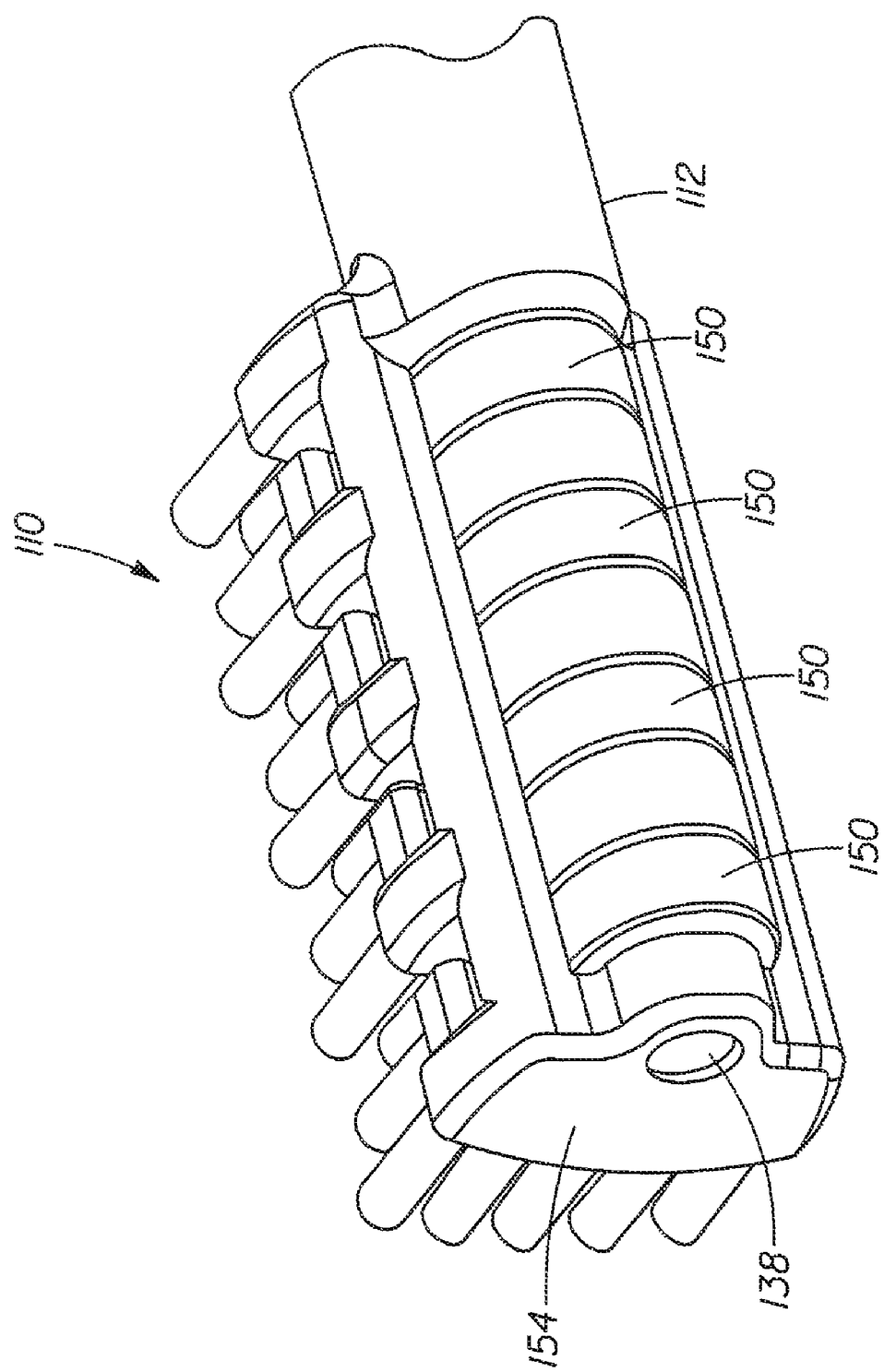
FIG. 6 is a schematic partial (bottom) perspective view of a brush head portion of the brush section illustrated in FIG. 5.

Referring to FIGS. 5-6 another embodiment of a brush section 110 is shown. Like elements of the brush section 110 to those of the brush section 10 are indicated using a reference numeral incremented by 100. The brush section 110 includes a mounting tube 112 extending along an axis 114. At a first end (not depicted), the mounting tube 112 is adapted to be push-fitted onto a handle section in a manner preventing relative rotation, as discussed previously with regard to the mounting tube 12.

At a second end 120 the brush section 110 includes a brush head portion 122. The brush head portion 122 supports a first plurality of contact elements 124 that are mounted to the head portion 122 so as to be fixed, i.e., static relative to the head portion 122. Any suitable method of mounting the first plurality of contact elements 124 to the head portion 122 may be used, such as those methods discussed heretofore with regard to the first plurality of contact elements 24. Supported within the head portion 122 is a movable contact element support or moveable contact element holder 126 supporting a second plurality of contact elements 128. The second plurality of contact elements 128 may be mounted to the movable contact element holder 126 using any suitable method, such as those discussed heretofore with regard to the second plurality of contact elements 28. The movable contact element holder 126 may be supported within the head portion 122 such that the movable contact element holder 126 is able to rotate about the axis 114 responsive to a suitable driving input from a handle section.

The first plurality of contact elements 124 may have a first height and the second plurality of contact elements 128 may have a second height, different than the first height. Additionally, the ends of the first and second pluralities of contact elements 124 and 128 may have contoured, rounded or otherwise shaped ends. Among the first plurality of contact elements 124 and the second plurality of contact elements 128, contact elements at different locations of the head portion 122 front to back and center to edge may also have different heights and different end contours. The first plurality of contact elements 124 may be arranged in rows transverse relative to the axis 114. Similarly, the second plurality of contact elements 128 may be arranged in rows transverse relative to the axis 114.

As shown in FIG. 6, the movable contact elements holder 126 may include a plurality of separately moveable contact element holder portions 150, each supporting a portion of the second plurality of contact elements 128. For example, each contact element holder portion 150 may support a separate transverse row of the second plurality of contact elements 128. The drive shaft 138 may extend through the head portion 122 and may be rotatably supported in an end member 154. The drive shaft 138 can be adapted to engage a drive member of a handle portion to which the brush section 110 is configured to operatively couple. Each movable contact element holder portion 150 may couple to the drive shaft 138 such that oscillation of the drive shaft 138 causes a like oscillation of the respective contact element portion 150. Each contact element holder portion 150 may be snap-fitted into the head portion 122 via an aperture 142 (shown in FIG. 7) and engaged with the drive shaft i38. A housing member (not depicted) may be provided to enclose the aperture 142. Additionally, the contact element holder portions 150 may be snap-fitted from a front side of the head portion 122.

As noted, each contact element holder portion 150 may be linked directly to the drive shaft 138 and thus to have an oscillating angular cleaning motion. Alternatively, at least some of the contact element holder portions 150 may be coupled by a linkage, cam structure or the like such that the contact element holder portion 150 has a cleaning motion separate from a rotating motion of the drive shaft 138 and/or a separate cleaning motion from other contact element holder portions 150.

Figure 7:
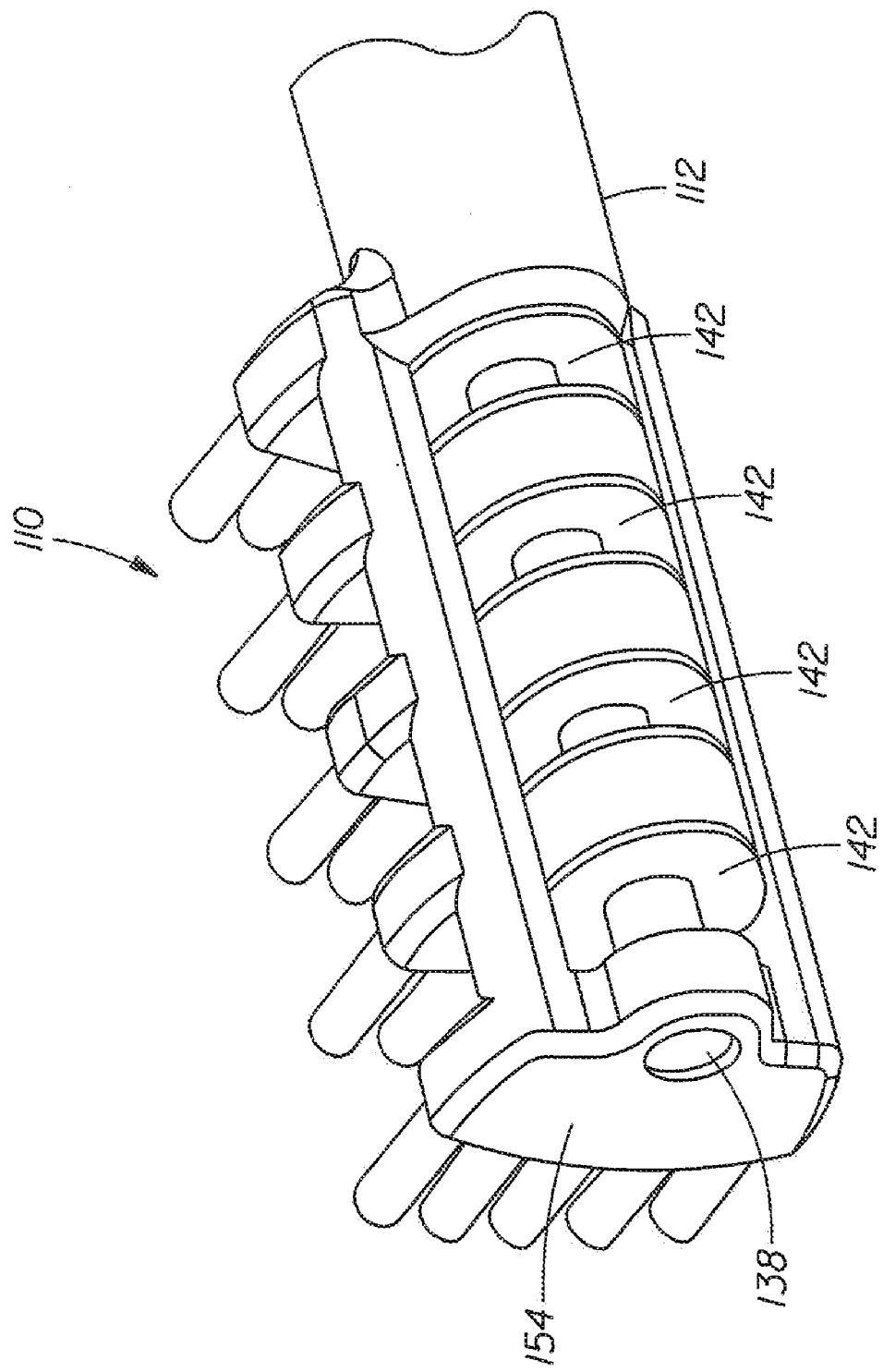
FIG. 7 is a schematic partial (bottom) perspective view of the brush head portion of FIG. 6 with the contact element holder portions removed for visual facilitation.

In the embodiment shown if FIGS. 5-7, each of the second plurality of contact elements 128 may be driven to oscillate back and forth angularly about the axis 114 to provide a cleaning action simulating an up-down manual brushing action. The second plurality of contact elements 128 may move through an angle of about 44 degrees, +/−22 degrees relative to the head portion 122. However, other angles greater than 44 degrees or less than 44 degrees may be used. In the embodiments described in FIGS. 5-7, any suitable angle may be utilized similar to those disclosed heretofore with regard to FIGS. 1-4.

In a similarly advantageous manner, the cleaning movement of the second plurality of contact elements 128 and a manually imparted cleaning movement of the head portion 122 by the user may provide an enhanced and effective cleaning action without drawing away from or degrading the driven cleaning action. The brush section 110 is also easily used in the same manner as a manual toothbrush to affect cleaning.

It is noted with respect to the brush section 110 that at least some of the contact element holder portions 150 may be separately coupled to the drive shaft 138 via a linkage, cam or similar structure to have a cleaning motion separate from a oscillating motion of the drive shaft 138. For example, as shown in FIG. 8, the drive shaft 138 may comprise a plurality of cams 160 offset from or eccentric relative to the axis 114. In some embodiments, each bristle holder portion 150 may be rotatably supported by engagement of a circular aperture 162 with a pin 166 formed on a static bristle support 164, a plurality of which, potentially corresponding to the number of rows of the first plurality of bristles 124, may be formed on the head section 122. Each cam 160 may engage a slot 168 formed in the bristle support portion 150 such that rotation of the drive shaft 138 causes a back and forth angular rotation of the bristle support portion 150 and the associated second plurality of bristles 128. Arrangement of the cams 160 on the drive shaft 138 permits each bristle holder portion 150 to have a separate rotating motion, which may enhance the cleaning action of the head section 122.

Advantageously, a complex drive motion of the drive shaft 138 may be avoided, as it may be driven in rotation with the action of the cam 160 engaging the bristle support portion 150 to provide the desired cleaning motion for the second plurality of bristles 128. For example, some embodiments may utilize a drive shaft which oscillates back and forth about the axis 114 to achieve the oscillatory motion of the first plurality of contact elements, the second plurality of contact elements, and/or the third plurality of contact elements. As yet another example, some embodiments, may utilize a drive shaft which rotates about the axis 114 to achieve the oscillatory motion of the first plurality of contact elements, the second plurality of contact elements, and/or the third plurality of contact elements.

As shown in FIG. 9, an alternate arrangement of the bristle holder portions 150, designated as bristle holder portions 150' is contemplated. As shown, each bristle holder portion 150' may be rotatably supported on the pin 166. However, instead of being formed with a circular aperture 162 (shown in FIG. 8), the bristle holder portion 150' may be formed with a slot 162' which engages the pin 166. Additionally, the slot 168 (shown in FIG. 8) may be formed as a circular opening 168' within which the cam 160 rotates with rotation of the drive shaft 138. Rotation of the drive shaft 138 causes a back and forth angular rotation of the bristle support portion 150' and the associated second plurality of bristles 128. Additionally, the bristle support portions 150' may be driven linearly along the slot 162' relative to the axis 114. This arrangement of bristle support portions 150' permits each bristle holder portion 150' to have a rotating and translating motion, which may enhance the cleaning action of the head section 122. Also, arrangement of the cams 160 on the drive shaft 138 may allow each individual bristle holder portion 150' to have a motion separate and distinct from each other bristle holder portion 150'. The resulting relatively complex cleaning motion may be imparted to the second plurality of bristles 128 without a complex drive motion of the drive shaft 138, which may be driven in rotation.

Figure 10:
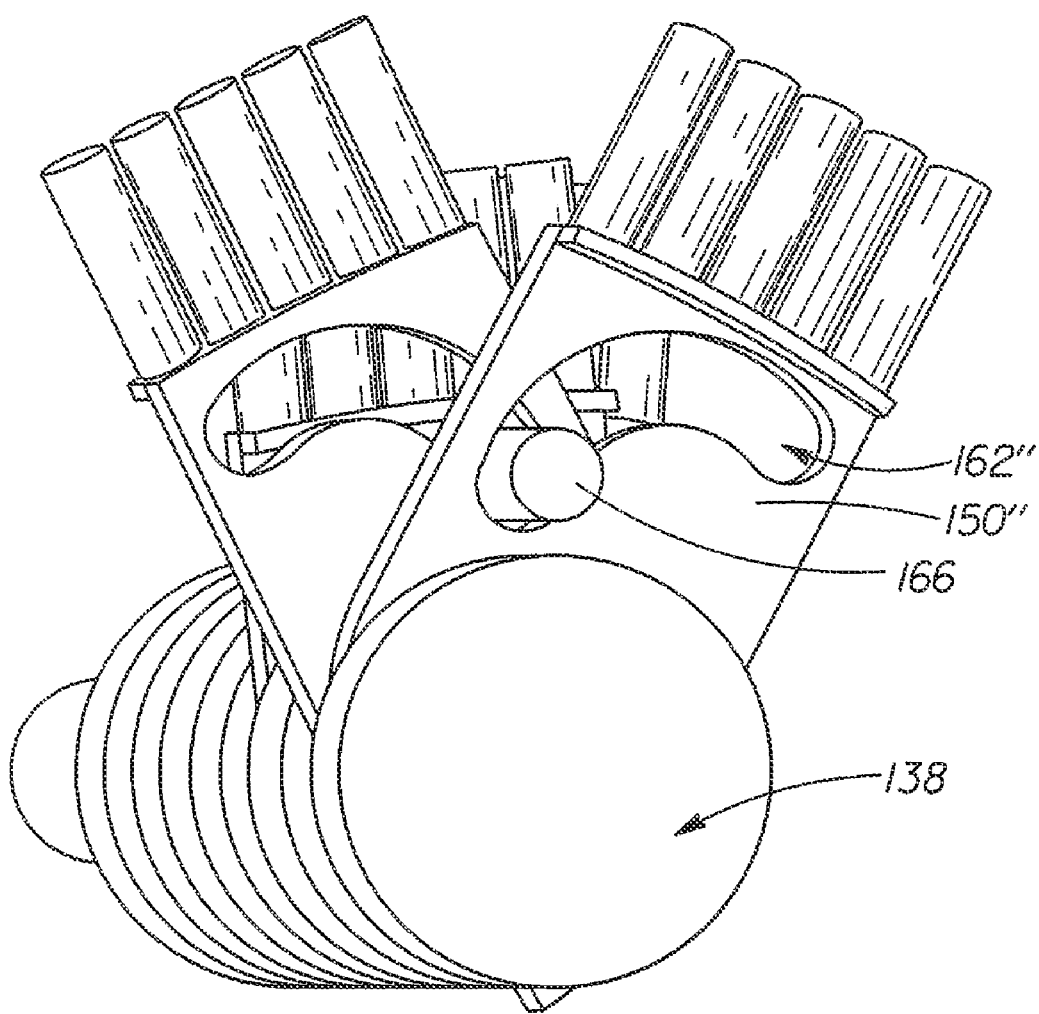
FIG. 10 is a schematic partial perspective view of a still further alternate brush head arrangement.

FIG. 10 illustrates yet another alternate arrangement of the bristle holder portions 150, designated as bristle holder portions 150". Each bristle holder portion 150" may be formed with an arcuate slot 162" that engages a corresponding pin 166 formed on a static bristle support. The drive shaft 138 may include eccentric cams such that rotation of the drive shaft 138 may provide rotating and translating motion of the bristle holder portions 150" via engagement of the drive shaft 138 with the respective bristle holder portions 150". Additionally, this arrangement may provide separate and distinct rotational and translation motion for each bristle holder portion 150" without a complex drive motion of the drive shaft 138.

As described, the various arrangements of a bristle holder portion, e.g., 150, 150' and 150", etc., permit relatively complex rotational and translational cleaning motions to be imparted to the second plurality of bristles 128. This may be accomplished with a simple rotating motion of the drive shaft 138 making brush sections 110 incorporating these configurations easily adaptable to existing handle section designs that may provide only for a rotating drive shaft output.

The first plurality of contact elements 24, the second plurality of contact elements 28, and/or the third plurality of contact elements 46 of the present invention may comprise a wide variety of materials and may have a number of different configurations. Any suitable material and/or any suitable configuration may be utilized.

For example, in some embodiments, the first plurality of contact elements 24, the second plurality of contact elements 28, and/or the third plurality of contact elements 46, may comprise tufts. The tufts may comprise a plurality of individual filaments which are securely attached to a cleaning element carrier. Such filaments may be polymeric and may include polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 cm to about 6 cm, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, a pointed tip. In some embodiments, the filaments may include a dye which indicates wear of the filaments as described in U.S. Pat. No. 4,802,255. Other suitable examples of filaments are described in U.S. Pat. No. 6,018,840. In some embodiments, the cleaning element fields may comprise fins as described in U.S. Pat. No. 6,553,604; U.S. Patent Application Publication Nos. 2004/0177462; 2005/0235439; and 2005/0060822. In some embodiments, the cleaning element fields may comprise a combination of fins and tufts.

Additionally, at least a portion of some of the first plurality of contact elements 24, the second plurality of contact elements 28, and/or the third plurality of contact elements 46 may be attached to a cleaning element carrier at an angle. Such orientations are described in U.S. Pat. No. 6,308,367. Also, any suitable method may be utilized to attach the first plurality of contact elements 24, the second plurality of contact elements 26, and/or the third plurality of contact elements 46 to their respective structures.

Embodiments are contemplated where the mounting tube 12, 112 (shown in FIGS. 1-3 and 5-9, respectively, is angled with respect to the handle section. In such embodiments, the drive shaft of the present invention may be provided in discrete portions thereby accommodating the angle of the mounting tube 12, 112. For example, the drive shaft may include one or more universal joints. As yet another example, the drive shaft may be constructed from a compliant material. Some examples of suitable materials for construction of the drive shaft include aluminum, spring steel, plastics, e.g. delrin, nylon, polypropylene, and/or combinations thereof.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be combined with or substituted for, in whole or part, any other feature, characteristic, component, composition, ingredient product, step or methodology described herein. Numerous alternative embodiments could be implemented, using either current technology or technology developed after the filing date of this patent, which would still fall within the scope of the claims.

What is claimed is:

1. A cleaning section for an electrical toothbrush with a handle section having a motor and a drive shaft, the cleaning section comprising:
   a single movable bristle holder structured to receive a drive motion from the motor via a drive mechanism comprising a drive shaft having a longitudinal axis, the drive shaft being structured to oscillate around its longitudinal axis thereby imparting rotation or oscillation to the single movable bristle holder; and
   a head including a first plurality of cleaning bristles arranged in a static bristle field which in use is static relative to the handle section and a second plurality of cleaning bristles arranged in a plurality of rows generally transverse to the longitudinal axis, wherein the second plurality of cleaning bristles are all supported within the single movable bristle holder to have at least one freedom of motion relative to the first plurality of cleaning bristles,
   wherein the single movable bristle holder is movable with respect to the head and the static bristle field such that a cleaning motion of the second plurality of cleaning bristles includes a back and forth oscillating movement of the second plurality of cleaning bristles about the longitudinal axis and relative to the first plurality of cleaning bristles, and wherein the back and forth oscillating movement of the second plurality of cleaning bristles is caused by the oscillating movement of the drive shaft.

2. The cleaning section of claim 1, wherein the first plurality of cleaning bristles are arranged in rows generally transverse to the longitudinal axis.

3. The cleaning section of claim 1, wherein the first plurality of cleaning bristles and the second plurality of cleaning bristles are arranged in rows generally transverse to a first axis of the head, the rows of the first plurality of cleaning bristles and the rows of the second plurality of cleaning bristles being interleaved.

4. The cleaning section of claim 1, wherein the first plurality of cleaning bristles and the second plurality of cleaning bristles are arranged in rows generally transverse to the longitudinal axis, the rows being alternate rows of the first plurality of cleaning bristles and the second plurality of cleaning bristles such that at least some of the rows of the second plurality of cleaning bristles are disposed between the rows of the first plurality of cleaning bristles, and at least some of the rows of the first plurality of cleaning bristles are disposed between the rows of the second plurality of cleaning bristles.

5. The cleaning section of claim 1, wherein the first plurality of cleaning bristles and the second plurality of cleaning bristles are arranged in rows generally transverse to the longitudinal axis, wherein every second row is a row of the first plurality of cleaning bristles.

6. The cleaning section of claim 1, wherein the cleaning motion comprises a reciprocating oscillation.

7. The cleaning section of claim 1, wherein the cleaning motion comprises an rotational and translational motion of the second plurality of cleaning bristles.

8. The cleaning section of claim 1, wherein the cleaning motion comprises oscillation of the second plurality of cleaning bristles about the longitudinal axis at a full oscillation angle of from approximately 40 degrees to approximately 60 degrees.

9. The cleaning section of claim 8, wherein the full oscillation angle is about 44 degrees.

10. The cleaning section of claim 8, wherein the full oscillation angle is about 55 degrees.

11. The cleaning section of claim 1, wherein the cleaning motion comprises an oscillation of the second plurality of cleaning bristles at a frequency of from about 80 Hz to about 120 Hz.

12. The cleaning section of claim 1, wherein the first plurality of cleaning bristles have a first bristle height and the second plurality of cleaning bristles have a second bristle height, different from the first bristle height.

13. An electric toothbrush comprising:
   a handle section including a motor, the handle section being coupled with a cleaning section, the cleaning section comprising a single movable bristle holder structured to receive a drive motion from the motor via a drive mechanism comprising a drive shaft having a longitudinal axis, the drive shaft being structured to oscillate around its longitudinal axis; and
   a head including a first plurality of cleaning bristles arranged in a static bristle field which in use is static relative to the handle section and a second plurality of cleaning bristles supported within the single movable bristle holder to have at least one freedom of motion relative to the first plurality of cleaning bristles, wherein the single movable bristle holder is movable with respect to the head and the static bristle field such that a cleaning motion of the second plurality of cleaning bristles includes an oscillating movement of the second plurality of cleaning bristles about the longitudinal axis relative to the first plurality of cleaning bristles, and wherein the oscillating movement of the second plurality of cleaning bristles is caused by the oscillating movement of the drive shaft;
   wherein the first plurality of cleaning bristles and the second plurality of cleaning bristles are arranged in rows that alternate such that at least some of the rows of the second plurality of cleaning bristles are disposed between the rows of the first plurality of cleaning bristles, and at least some of the rows of the first plurality of cleaning bristles are disposed between the rows of the second plurality of cleaning bristles; and wherein the rows of the second plurality of cleaning bristles are mounted to the single movable bristle holder.

14. A cleaning section for an electrical toothbrush with a handle section having a motor and a drive shaft, the cleaning section comprising:
   a single movable bristle holder structured to receive a drive motion from the motor via a drive mechanism comprising a drive shaft having a longitudinal axis, the drive shaft being structured to oscillate around its longitudinal axis thereby imparting rotation or oscillation to the single movable bristle holder; and
   a head including a first plurality of cleaning bristles arranged in a static bristle field which in use is static relative to the handle section and a second plurality of cleaning bristles supported within the single movable bristle holder to have at least one freedom of motion relative to the first plurality of cleaning bristles,
   wherein the single movable bristle holder is movable with respect to the head and the static bristle field such that a cleaning motion of the second plurality of cleaning bristles includes an oscillating movement of the second plurality of cleaning bristles about the longitudinal axis relative to the first plurality of cleaning bristles, and wherein the oscillating movement of the second plurality of cleaning bristles is caused by the oscillating movement of the drive shaft;
   wherein the first plurality of cleaning bristles and the second plurality of cleaning bristles are arranged in rows generally transverse to a first axis of the head, the rows of the first plurality of cleaning bristles and the rows of the second plurality of cleaning bristles being interleaved; and wherein the rows of the second plurality of cleaning bristles are mounted to the single movable bristle holder.

\* \* \* \* \*